United States Patent [19]

Wieland

[11] Patent Number: 4,609,482

[45] Date of Patent: Sep. 2, 1986

[54] WASHING AND CLEANING AGENT WITH ANTIMYCETIC ACTION

[75] Inventor: Carl P. Wieland, Hochwaldstrasse 41, Baldham, Fed. Rep. of Germany, D-8011

[73] Assignees: C. P. Wieland; C. Zillich, both of Munich, Fed. Rep. of Germany

[21] Appl. No.: 709,695

[22] PCT Filed: Jun. 4, 1984

[86] PCT No.: PCT/DE84/00124

§ 371 Date: Feb. 14, 1985

§ 102(e) Date: Feb. 14, 1985

[87] PCT Pub. No.: WO85/00041

PCT Pub. Date: Jan. 3, 1985

[30] Foreign Application Priority Data

Jun. 16, 1983 [DE] Fed. Rep. of Germany ....... 3321840

[51] Int. Cl.$^4$ ............................................. C11D 3/48
[52] U.S. Cl. ..................................... 252/106; 252/173; 252/542; 252/DIG. 5; 514/399; 514/859

[58] Field of Search ................ 252/106, 542; 514/399, 514/859

[56] References Cited

U.S. PATENT DOCUMENTS

| | | | |
|---|---|---|---|
| 3,658,813 | 4/1972 | Godefroi et al. | 260/240 K |
| 3,793,453 | 2/1974 | Godefroi et al. | 252/106 |
| 3,917,815 | 11/1975 | Kalopissis et al. | 252/106 |
| 4,505,924 | 3/1985 | Taylor et al. | 514/399 |

FOREIGN PATENT DOCUMENTS 2066075 7/1981 United Kingdom .

Primary Examiner—Paul Lieberman
Assistant Examiner—Hoa Van Le
Attorney, Agent, or Firm—Felfe & Lynch

[57] ABSTRACT

New compositions useful for washing or cleaning are disclosed. The compositions have antimycetic properties, and contain sodium lauryl sulphate and imazalil. The amounts of these may range from 10–40% sodium lauryl sulphate and 0.02 to 0.5% imazalil, and preferably contain 10–30% sodium lauryl sulphate and 0.02–0.2% imazalil.

7 Claims, No Drawings

WASHING AND CLEANING AGENT WITH ANTIMYCETIC ACTION

The invention concerns a washing and cleaning agent with antimycetic action.

Mycoses belong to the modern diseases of civilisation in the highly industrialised countries. According to recent estimates, every third citizen suffers from a skin or mucous membrane mycosis one or more times in the course of his life. Pharmaceuticals, such as antibiotics, cytostatics, contraceptives and immunosuppressives, favour the multiplication of fungi on the skin and mucous membranes of human. Other environmental influences, such as cosmetics and cigarette consumption, also contribute to a multiplication of fungi. Due to the keeping of domestic animals, especially house and amusement animals in large towns, the development of fungi in the immediate surroundings of humans is also favoured. Admittedly, effective medicaments are today available for the treatment of this type of fungal diseases but recidivation frequently occurs. This is due to the fact that admittedly the fungi and fungal spores are destroyed on the skin and the mucous membranes but the fungi in the human environment resist external influences and do not die off. Fungal spores in particular are very resistant and can, therefore, survive environmental influences harmful for other organisms.

Thus, with the known washing and cleaning agents, it is not possible to kill off fungi and fungal spores since fungi and especially their spores are often resistant to tensides.

A special problem arises from this that, on the one hand, many articles of clothing consist of materials which only permit a washing at low temperatures and, on the other hand, cleaning and rinsing agents can only be used at low temperatures.

Thus, it was the task of the invention to find an agent with which fungi and fungal spores in laundry and in human surroundings can also be killed off at temperatures below 100° C. This task was solved by a washing and cleaning agent with antimycetic action which is characterised in that, besides the usual component materials, it contains sodium lauryl sulphate and imazalil.

Conventional washing agents cannot completely kill off fungi and fungal spores at temperatures below 100° C. Surprisingly, it was not found that, by the addition of two synergistically-active active materials, the killing off of fungi and fungal spores is possible at lower temperatures, even below 60° C.

The washing and cleaning agent according to the invention is suitable also for killing off fungi and fungal spores on articles of clothing which cannot be boiled but can only be washed at 30° C. or 60° C. Furthermore, this agent is suitable for destroying fungi and fungal spores on articles in the case of cleaning.

For the killing off of the fungi and fungal spores, the agent should contain up to 40% sodium lauryl sulphate and up to 0.5% imazalil. By imazalil there is understood 1-[2-(2,4-dichlorophenyl)-2-(2-propenoxy)ethyl]-1H-imidazole.

Preferably, there is used an amount of 10 to 30% sodium lauryl sulphate. The fungicide imazalil is, due to the synergistic combination with sodium lauryl sulphate, only necessary in small amounts of up to 0.5%. An amount of 0.02 to 0.2% has been shown to be suitable in order still to ensure a 100% killing off of the fungi and fungal spores.

The ratio of sodium lauryl sulphate to imazalil is not critical. However, it has been shown that a ratio of sodium lauryl sulphate to imazalil of 1000:1 is still suitable to kill off 100% of the fungi and fungal spores. In the case of a ratio of 100:1, the solution furthermore still manifests a bactericidal action in the case of a germ content of 10 to 50 germs per ml. of liquor.

The agent according to the invention is suitable for use as washing agent, as cleaning agent and as rinsing agent. The special properties of the agent according to the invention make it possible to use this agent as washing agent for laundry at low temperatures. The killing off of micro-organisms and fungi in boiled laundry is no problem since these organisms are not able to survive boiling temperatures. However, there is a problem in the case of clothing of wool, silk, synthetic fabrics or also dyed fabrics. All these materials only withstand washing temperatures of 30° C. or 60° C. However, precisely stockings and laundry, which consist of wool or synthetic fabrics, are to be feared as transmitters of fungi. With the help of the agent according to the invention, it is now possible also to kill off fungi and fungal spores in these articles of clothing and thus to ward off otherwise transmittable infections.

Also in the case of the cleaning of articles which continuously come into contact with the human skin, it was previously not possible to kill of fungi and fungal spores. Conventional cleaning agents which can certainly only be used at low temperatures in order not to cause scorching in the case of use could not lead to a satisfactory killing off of the fungi and fungal spores. However, the agent according to the invention permits the killing off of fungi and fungal spores even in the environment of humans and thus, here too, precludes the possibility of transmission of fungal diseases.

The transmission of fungi and fungal spores via crockery and especially via vessels used by domestic animals is a further possibility of infection. Here, too, the agent according to the invention acts due to its special properties. Rinsing agents can also only be used at low temperatures in order not to lead to scorching in the case of rinsing. With the help of the agent according to the invention, which also acts at low temperatures, it is now possible also so to rinse crockery that it no longer carries fungi and fungal spores capable of infection.

Thus, according to the invention, a washing and cleaning agent is made available which manifests its antimycetic action even at low temperatures. Due to its possibilities of use, even for cleaning and rinsing, it is thus suitable to make human surroundings free of fungi and fungal spores.

The following Examples explain the invention.

EXAMPLE 1

20% Sodium lauryl sulphate and 0.02% imazalil were added to a conventional washing agent. This agent was tested according to the test directions for the testing of disinfection agents of the Deutsche Gesellschaft für Hygiene und Mikrobiologie (German Society for Hygiene and Microbiology) and of the Deutsche veterinärmedizinische Gesellschaft (German veterinary-medical Society) with *Candida albicans* and *Trichophyton mentagrophytes* as test micro-organisms. The time of action and the temperature were adapted to the parameters prevailing in the case of the washing procedure. There was obtained a 100% killing of the germs.

COMPARATIVE EXAMPLE

20% Sodium lauryl sulphate was added to a conventional washing agent and tested as in Example 1. There was obtained a residual germ content of 1 to 10 fungal spores per ml. of wash liquor.

EXAMPLE 2

20% Sodium lauryl sulphate and 0.02% imazalil was added to a conventional liquid washing agent. The solution was tested as in Example 1. It showed a 100% fungicidal action.

EXAMPLE 3

A solution was prepared from a conventional washing agent with 20% sodium lauryl sulphate and 0.2% imazalil. Then, according to the test directions mentioned in Example 1, there was also tested with Staphylococcus aureus, which had proved to be detergent-resistant, as test germ. It showed that, in the case of a germ content of 10 to 50 germs per ml. of wash liquor, the solution manifested a bactericidal action.

SUMMARY

A washing and cleaning agent with antimycetic action contains, besides the conventional component materials, sodium lauryl sulphate and imazalil.

I claim:

1. Washing and cleansing agent with antimycetic action comprising from about 10% to about 40% sodium lauryl sulphate and from about 0.02 to about 0.5% imazalil.

2. Agent according to claim 1, characterised in that it contains 10 to 30% sodium lauryl sulphate.

3. Agent according to claim 1, characterized in that it contains 0.02 to 0.2% imazalil.

4. Method of washing or cleaning comprising washing or cleaning an object with a composition comprising from about 10% to about 40% sodium lauryl sulphate and from about 0.02 to about 0.5% imazalil.

5. Method of claim 4, wherein said composition comprises 10% to 30% sodium lauryl sulphate.

6. Method of claim 4, wherein said composition comprises 0.02% to 0.2% imazalil.

7. Method of claim 4, wherein said washing or cleaning is performed at a temperature of from about 30+ to about 60° C.

* * * * *

UNITED STATES PATENT AND TRADEMARK OFFICE
CERTIFICATE OF CORRECTION

PATENT NO. : 4,609,482

DATED : September 2, 1986

INVENTOR(S) : Carl P. Wieland

It is certified that error appears in the above-identified patent and that said Letters Patent is hereby corrected as shown below:

Column 1, line 47: change "not" to -- now --;

line 48: change "active", first occurrence to -- acting --.

Claim 7, line 2: change "30" to -- 30° --.

Signed and Sealed this

Sixth Day of January, 1987

*Attest:*

DONALD J. QUIGG

*Attesting Officer*   *Commissioner of Patents and Trademarks*